(12) United States Patent
Barker et al.

(10) Patent No.: US 11,957,844 B2
(45) Date of Patent: Apr. 16, 2024

(54) WATER OUT ALARM

(71) Applicant: Fisher & Paykel Healthcare Limited, Auckland (NZ)

(72) Inventors: Dean Antony Barker, Auckland (NZ); Jack Che-Wei Hsu, Auckland (NZ); Jae Chul Han, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 18/308,565

(22) Filed: Apr. 27, 2023

(65) Prior Publication Data

US 2023/0330381 A1   Oct. 19, 2023

Related U.S. Application Data

(60) Continuation of application No. 16/704,360, filed on Dec. 5, 2019, now Pat. No. 11,679,227, which is a (Continued)

(51) Int. Cl.
*A61M 16/16* (2006.01)
*A61M 16/00* (2006.01)
(Continued)

(52) U.S. Cl.
CPC ........ *A61M 16/16* (2013.01); *A61M 16/0051* (2013.01); *A61M 16/0057* (2013.01);
(Continued)

(58) Field of Classification Search
CPC .............. A61M 16/16; A61M 16/0069; A61M 16/109; A61M 16/1095; A61M 16/127;
(Continued)

(56) References Cited

U.S. PATENT DOCUMENTS 3,982,098 A   9/1976   Trostler
4,676,237 A   6/1987   Wood et al.
(Continued)

FOREIGN PATENT DOCUMENTS

CN   1667400 A   9/2005
CN   101112637 A   1/2008
(Continued)

OTHER PUBLICATIONS

International Search Report; PCT/NZ2011/000058, dated Jul. 18, 2011; 5 pages.

*Primary Examiner* — Charles S Bushey
(74) *Attorney, Agent, or Firm* — Knobbe, Martens, Olson & Bear, LLP

(57) ABSTRACT

The present invention provides for an improved method of determining a water out condition in a humidified gases supply apparatus. The method includes a two step process including a primary determination of a water out condition and a secondary determination of a water out condition. This primary determination is made during observation of the normal operation of the apparatus. During the secondary determination the method takes temporary control over the humidifying part of the apparatus. The secondary determination confirms or contradicts the primary determination.

20 Claims, 9 Drawing Sheets

Related U.S. Application Data division of application No. 15/174,485, filed on Jun. 6, 2016, now Pat. No. 10,532,178, which is a continuation of application No. 13/643,901, filed as application No. PCT/NZ2011/000058 on Apr. 26, 2011, now Pat. No. 9,393,379.

(60) Provisional application No. 61/328,548, filed on Apr. 27, 2010.

(51) Int. Cl.
| | |
|---|---|
| *A61M 16/06* | (2006.01) |
| *A61M 16/08* | (2006.01) |
| *A61M 16/10* | (2006.01) |
| *A61M 16/12* | (2006.01) |
| *A61M 16/20* | (2006.01) |
| *H05B 1/02* | (2006.01) |

(52) U.S. Cl.
CPC .... *A61M 16/0066* (2013.01); *A61M 16/0069* (2014.02); *A61M 16/024* (2017.08); *A61M 16/0666* (2013.01); *A61M 16/0875* (2013.01); *A61M 16/1075* (2013.01); *A61M 16/109* (2014.02); *A61M 16/1095* (2014.02); *A61M 16/127* (2014.02); *A61M 16/161* (2014.02); *A61M 16/20* (2013.01); *H05B 1/025* (2013.01); *A61M 2016/0021* (2013.01); *A61M 2016/0027* (2013.01); *A61M 2016/003* (2013.01); *A61M 2016/0039* (2013.01); *A61M 16/0841* (2014.02); *A61M 16/162* (2013.01); *A61M 2202/0208* (2013.01); *A61M 2205/18* (2013.01); *A61M 2205/3368* (2013.01); *A61M 2205/3379* (2013.01)

(58) Field of Classification Search
CPC .............. A61M 16/161; A61M 16/024; A61M 16/0051; A61M 16/0057; A61M 16/0066; A61M 16/0666; A61M 16/0875; A61M 16/1075; A61M 16/20; A61M 16/0841; A61M 16/162; A61M 2016/0021; A61M 2016/0027; A61M 2016/003; A61M 2016/0039; A61M 2202/0208; A61M 2205/18; A61M 2205/3368; A61M 2205/3379; H05B 1/025
USPC ....... 261/127, 128, 129, 130, 131, 142, 152, 261/DIG. 65; 128/203.14
See application file for complete search history.

(56) References Cited

U.S. PATENT DOCUMENTS

| | | |
|---|---|---|
| 5,679,274 A | 10/1997 | Mahood |
| 6,349,722 B1 | 2/2002 | Gradon et al. |
| 6,649,881 B2 | 11/2003 | Scott et al. |
| 6,802,314 B2 | 10/2004 | McPhee |
| 6,895,803 B2 | 5/2005 | Seakins et al. |
| 7,099,572 B2 | 8/2006 | Phillips |
| 7,306,205 B2 | 12/2007 | Huddart et al. |
| 7,473,868 B2 | 1/2009 | Bohan et al. |
| 8,739,780 B2 | 6/2014 | Tang et al. |
| 8,893,715 B2 | 11/2014 | Payton et al. |
| 9,168,350 B2 | 10/2015 | Payton et al. |
| 9,393,379 B2 | 7/2016 | Barker et al. |
| 9,440,042 B2 | 9/2016 | McAuley et al. |
| 10,532,178 B2 | 1/2020 | Barker et al. |
| 11,679,227 B2 * | 6/2023 | Barker .............. A61M 16/0051 128/203.14 |
| 2002/0139367 A1 | 10/2002 | McPhee |
| 2004/0079370 A1 | 4/2004 | Gradon et al. |
| 2004/0244804 A1 | 12/2004 | Olsen et al. |
| 2008/0190427 A1 | 8/2008 | Payton et al. |
| 2009/0184832 A1 | 7/2009 | Lloyd et al. |
| 2011/0125052 A1 | 5/2011 | Davenport et al. |
| 2011/0168690 A1 * | 7/2011 | Tomomura ............... A21B 3/04 219/401 |
| 2013/0174841 A1 | 7/2013 | McAuley et al. |
| 2020/0129725 A1 | 4/2020 | Barker et al. |

FOREIGN PATENT DOCUMENTS

| | | |
|---|---|---|
| CN | 101203073 A | 6/2008 |
| GB | 2185161 A | 7/1987 |
| WO | WO 2005/011556 | 2/2005 |
| WO | WO 2011/078706 | 6/2011 |

* cited by examiner

WATER OUT ALARM

CROSS-REFERENCE TO RELATED APPLICATIONS

This application is a continuation of U.S. patent application Ser. No. 16/704,360, filed Dec. 5, 2019, now U.S. Pat. No. 11,679,227, which is a divisional of U.S. patent application Ser. No. 15/174,485, filed Jun. 6, 2016, now U.S. Pat. No. 10,532,178, issued Jan. 14, 2020, which is a continuation of U.S. patent application Ser. No. 13/643,901, filed Jan. 17, 2013, now U.S. Pat. No. 9,393,379, issued Jul. 19, 2016, which is a national phase of International Application No. PCT/NZ2011/000058, filed Apr. 26, 2011, which claims priority from U.S. Provisional Application No. 61/328,548, filed Apr. 27, 2010.

BACKGROUND OF THE INVENTION

Field of the Invention

The present invention relates to humidification systems for gases to be supplied to a patient.

Description of the Related Art

For a range of applications, it is now known to be beneficial to humidify gases being supplied to a patient. These applications include where the gases are for breathing by the patient and where the gas is being supplied during surgery to the patient. In the case of breathing gases, the humidity increases patient comfort and the humidified gases are less prone to drying out the tissues of the patient airway. In the case of surgical gases, the humidified gases reduce the drying out of exposed tissue and improve post operative outcomes.

In a gases humidification system incorporating a humidification chamber for humidifying gases for supply to the patient, it is important that a certain minimum level of water is maintained in order for the humidifier to have the ability to supply water vapour to the gases flow. Accordingly, the healthcare professional administering the humidified gases to the patient, or the patient themselves, in the case of home-based administration, should occasionally check the water level and add more water when required. This task is sometimes overlooked.

U.S. Pat. No. 6,802,314 describes a respiratory humidification system which automatically determines when the water level drops to an insufficient level and raises an alarm. The system calculates, continuously, a measure of thermal conductivity as the power input divided by the difference between the heater plate temperature and the temperature of the gases exiting the humidifier chamber. The controller compares the calculated thermal conductivity with a predetermined threshold value suitable for the flow rate of gases in the system. If the thermal conductivity is less than the threshold value, the controller activates an alarm.

This respiratory humidification system is intended for an environment having fairly consistent ambient conditions. For example, hospital wards, where these devices are most frequently used, tend to be air-conditioned and maintained at a comfortable temperature and background humidity.

Another example of an alarm system for alerting a user to replenish a humidifying chamber is described in US patent application 2009/0184832. This patent application describes a humidifier for use in surgical insufflation. According to one embodiment, a controller measures the total power input to the humidifier heater over time. According to the applicant, this represents the evaporation of a proportional amount of water from the reservoir. Once the total work (accumulated power over a period of time beginning when the chamber was filled) reaches a predetermined level, the controller indicates to the user that the humidifier chamber may need refilling. In a further aspect described, the threshold level can be selected according to the temperature of the gases entering the system. According to another aspect, the system determines that hydration fluid needs to be re-charged by determining whether the instantaneous power drops below a threshold, which could be different for different flow rates or ranges of flow rates. According to another variation, the controller monitors the temperature signal of the conditioned gas approximate or inside the heater hydrator and activates an alarm when the temperature signal of the insufflation gas begins to vary significantly.

A still further system is described in U.S. application 61/289,610, filed 23 Dec. 2009 and assigned to Fisher & Paykel Healthcare Limited. This also describes a humidification system for gases used in insufflation or open-wound surgery. According to this application, a condition of low or no water in the humidifier chamber is detected by monitoring the temperature of gases exiting the chamber while monitoring the power supply to the heater base. If the temperature of the gases exiting the chamber drops at the same time as the power supplied to the heater is constant or increasing, the controller determines this as a water-out condition and alerts a user.

The surgical systems also operate within well-defined ambient conditions. For example, they are typically used in operating theatres maintained at a regulated cool temperature and in an air-conditioned environment with relatively constant ambient humidity.

The inventors consider that each of the aforementioned systems is susceptible to false alarms. They are susceptible to determining that there is an absence of water in the chamber, and alerting the healthcare professional to this condition, in situations where the chamber is not actually empty. While an accidental false alarm is not critical in a situation where the system is being used by trained healthcare professionals, they are unhelpful in situations where the humidified gases delivery systems are being used outside the controlled hospital environment. Systems used outside the controlled hospital environment may also be more susceptible to false alarms due to the wider range of ambient conditions in which they operate with ambient temperatures ranging, for example, from 12° C. to 32° C., and ambient humidity also widely varied. The varied ambient conditions are typical if the device is used in the home environment, such as devices used in CPAP therapy or oxygen therapy.

SUMMARY OF THE INVENTION

It is an object of the present invention to provide a gases humidification system which at least goes some way towards overcoming the above disadvantages, which will at least provide the industry with a useful choice.

In one aspect, the present invention consists in an apparatus for preparing a flow of gases including a heater for heating a reservoir, a temperature sensor in thermal communication with the heater to read the temperature of the heater, a controller adapted to apply power from a power supply to the heater, the controller including a control method comprising monitor system conditions during use of the apparatus, determine a possible absence of water in the reservoir from the monitored system conditions, following a determination of a possible absence of water, apply power from the power supply to the heater, the amount of power being an increase in the supplied power, a maximum power from the power supply to the heater, a predetermined amount of power from the power supply to the heater; or an amount of power to the heater that would elevate the heater temperature in the absence of water, to a temperature that exceeds any temperature that the heater temperature would reach with water present in the chamber, monitor the output of the temperature sensor, and reduce the power supplied from the power supply to the heater, removing power from the heater completely if the monitored temperature sensor output indicated an absence of water in the reservoir.

According to a further aspect, the step of monitoring the output of the temperature sensor includes determining a rise in heater plate temperature.

According to a further aspect, the step of monitoring the output of the temperature sensor includes comparing the heater temperature against a threshold temperature and determining a water out condition where the monitored temperature exceeds the predetermined threshold temperature.

According to a further aspect, the controller determines the water out condition when the monitored temperature exceeds the predetermined threshold temperature by a predetermined period of time.

According to a further aspect, the step of applying power to the heater comprises applying a maximum available power to the heater.

According to a further aspect, the step of applying power to the heater comprises applying a predetermined amount of power to the heater.

According to a further aspect, the step of applying power to the heater comprises applying an amount of power to the heater that would elevate the heater temperature in the absence of water to a temperature that exceeds any temperature that the heater temperature would reach with water present in the chamber.

According to a further aspect, the heater comprises a heater plate and the apparatus includes a clamp for holding a removable chamber against the heater plate.

According to a further aspect, the temperature sensor is attached to the heater plate.

According to a further aspect, the apparatus for preparing a flow of gases includes a blower for generating a flow of gases and a humidifier incorporating the heater and a reservoir of water, an outlet of the blower leading to an inlet of the humidifier.

According to a further aspect, the controller monitors system conditions during use of the apparatus including monitoring the temperature of gases leaving the reservoir and monitoring power applied to the heater and determines a possible water out condition based on a function of the temperature of gases leaving the humidifier and the power applied to the heater.

According to a further aspect, the function comprises a ratio of the gases temperature to the heater plate power.

According to a further aspect, the controller determines a possible absence of water in the reservoir by comparing the result of the function against a predetermined threshold.

In a further aspect, the present invention consists in an apparatus for preparing a flow of gases including a humidifier including a reservoir and a heater for heating the reservoir, a temperature sensor in thermal communication with the heater to read the temperature of the heater, a controller adapted to apply power from a power supply to the heater, the controller including a control method comprising monitor system conditions during use of the apparatus, determine a possible absence of water in the reservoir from the monitored system conditions, following a determination of a possible absence of water, applying a maximum available power from the power supply to the heater, monitor the output of the temperature sensor, determining a water out condition if the output of the temperature sensor exceeds a predetermined threshold for a predetermined period of time, subsequently reducing the power supplied from the power supply to the heater, and providing an output indicating the water out condition To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The term "comprising" is used in the specification and claims, means "consisting at least in part of". When interpreting a statement in this specification and claims that includes "comprising", features other than that or those prefaced by the term may also be present. Related terms such as "comprise" and "comprises" are to be interpreted in the same manner.

BRIEF DESCRIPTION OF THE DRAWINGS

Preferred embodiments of the present invention will be described with reference to the accompanying drawings.

DETAILED DESCRIPTION OF THE PREFERRED EMBODIMENT

Figure 1:
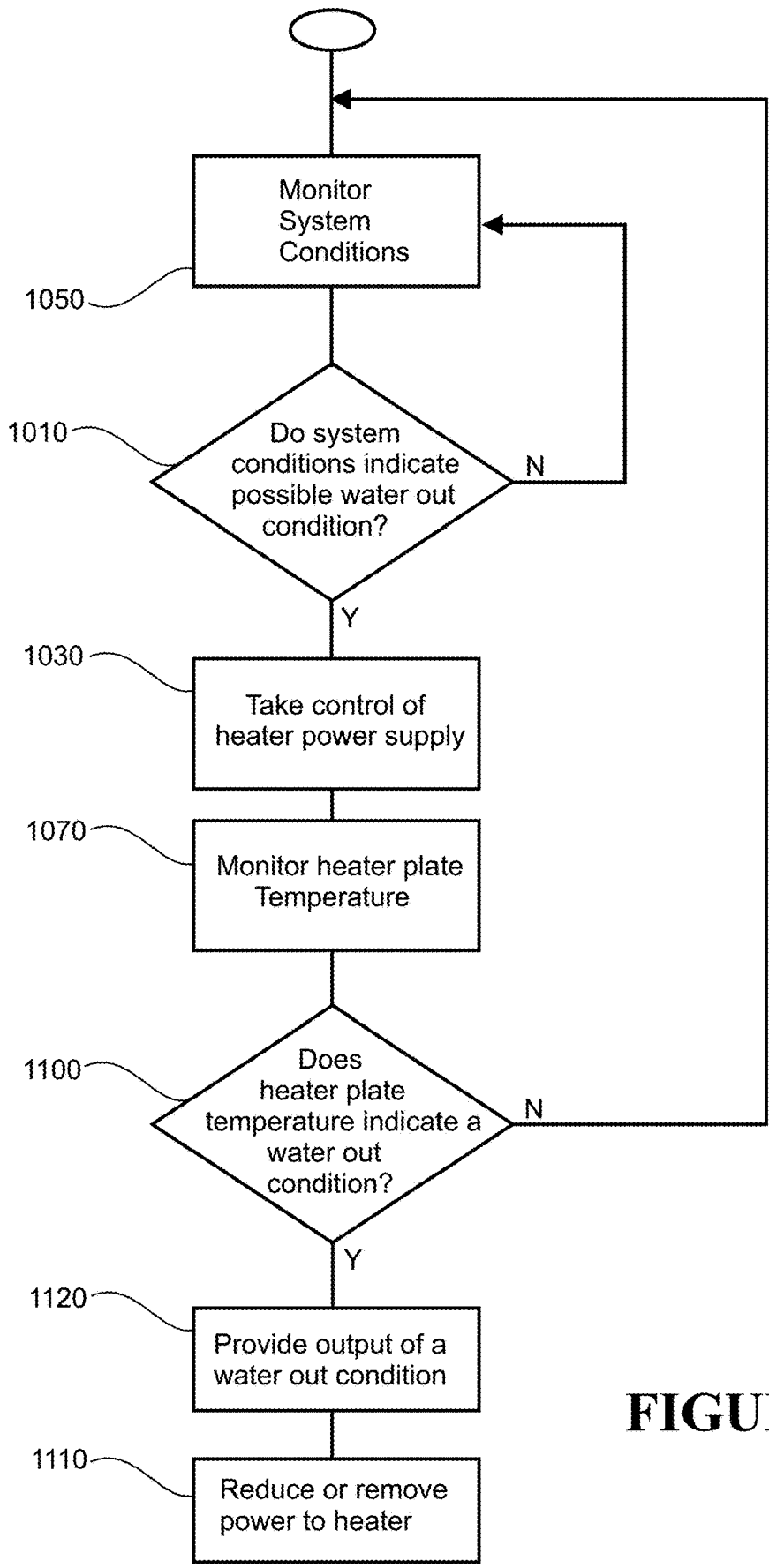
FIG. 1 is a flow diagram illustrating the overall process for determining an absence of water in a humidifier chamber in accordance with the present invention.

The present invention provides for an improved method of determining a water out condition in a humidified gases supply apparatus. This method has been found suitable for determining water out conditions in widely varying ambient conditions. As illustrated in FIG. 1, the method includes a two step process including a primary determination of a water out condition at step 1010. This primary determination is made during observation (at step 1050) of the normal operation of the apparatus. Following a primary determination of a water out condition the method takes temporary control over the humidifying part of the apparatus at step 1030 to make a secondary determination at step 1100 which will confirm or contradict the primary determination.

For the primary determination, the controller of the apparatus may monitor a range of characteristics of the system, as sensed by one or more of the sensors included in the system. For example, the primary determination may be made by any one of a number of prior art methods described discussed in the background discussion. However, a preferred method for the primary determination monitors a function of the chamber outlet temperature and the heater plate temperature and determines the possibility of a water out condition when this function moves away from a base line value.

According to a preferred aspect of the present invention, the secondary determination, interrupts the normal control of the apparatus and takes over control of the humidifier heater power input. According to the method for the secondary determination the heater power is increased to a maximum available value for a limited period of time. The secondary determination is then made based on the monitoring heater plate temperature (at step 1070). This determination may be on the basis of the heater plate temperature rising steeply during this time or staying at an elevated level during this time, or reaching an elevated level during this time indicative of a water out condition.

The controller can then provide output of the water out condition (step 1120) to activate a user alert. The controller also reduces or removes power to the heater plate (step 1110).

The water out determination method according to the present invention has been developed with particular application to humidified gases delivery apparatus used outside the hospital environment. However, the method may also find beneficial in controllers for apparatus intended for the hospital environment.

Figure 3:
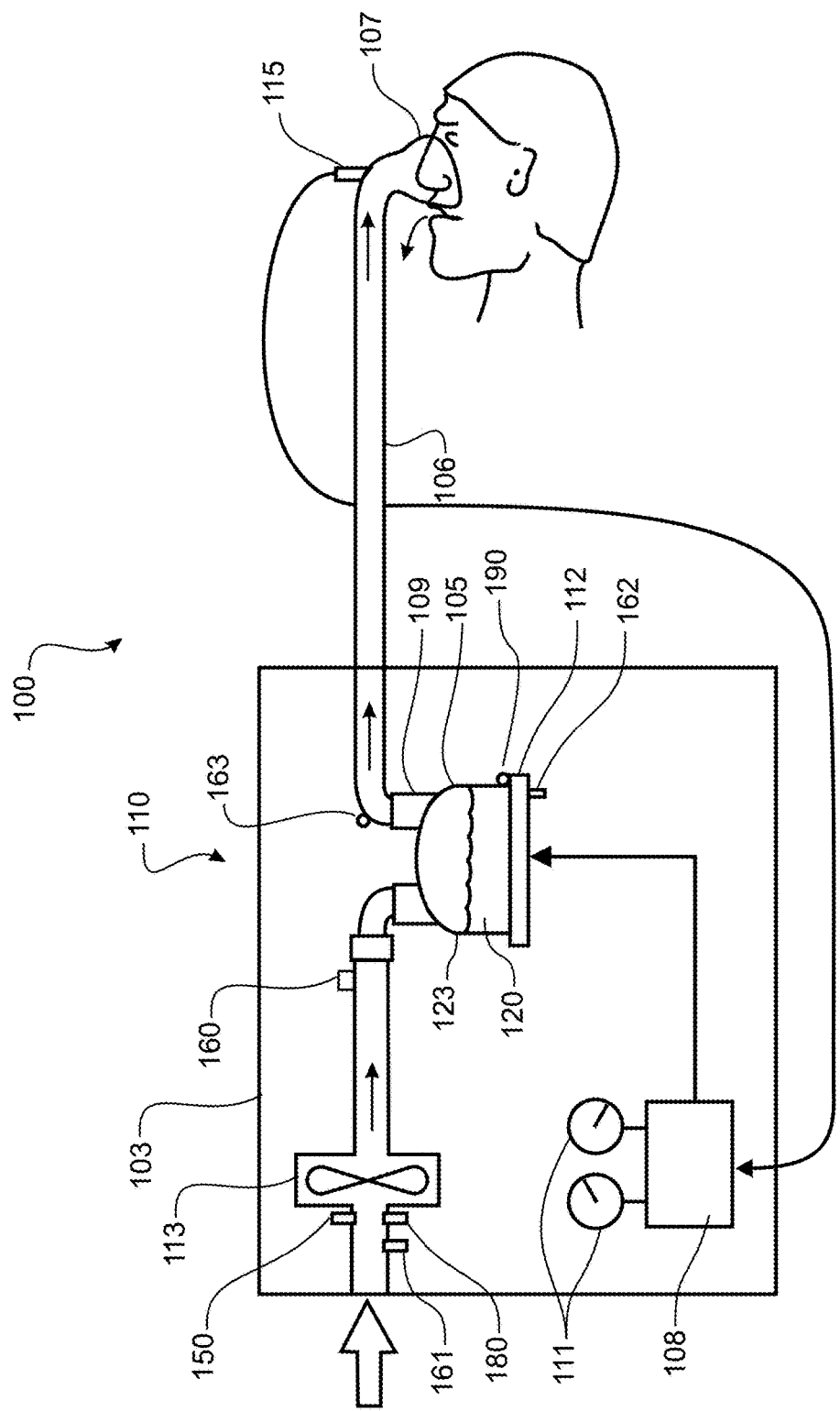
FIG. 3 shows a schematic view of a user receiving humidified air, where the user is wearing a nasal mask and receiving air from an integrated blower/humidifier breathing assistance system.
Figure 4:
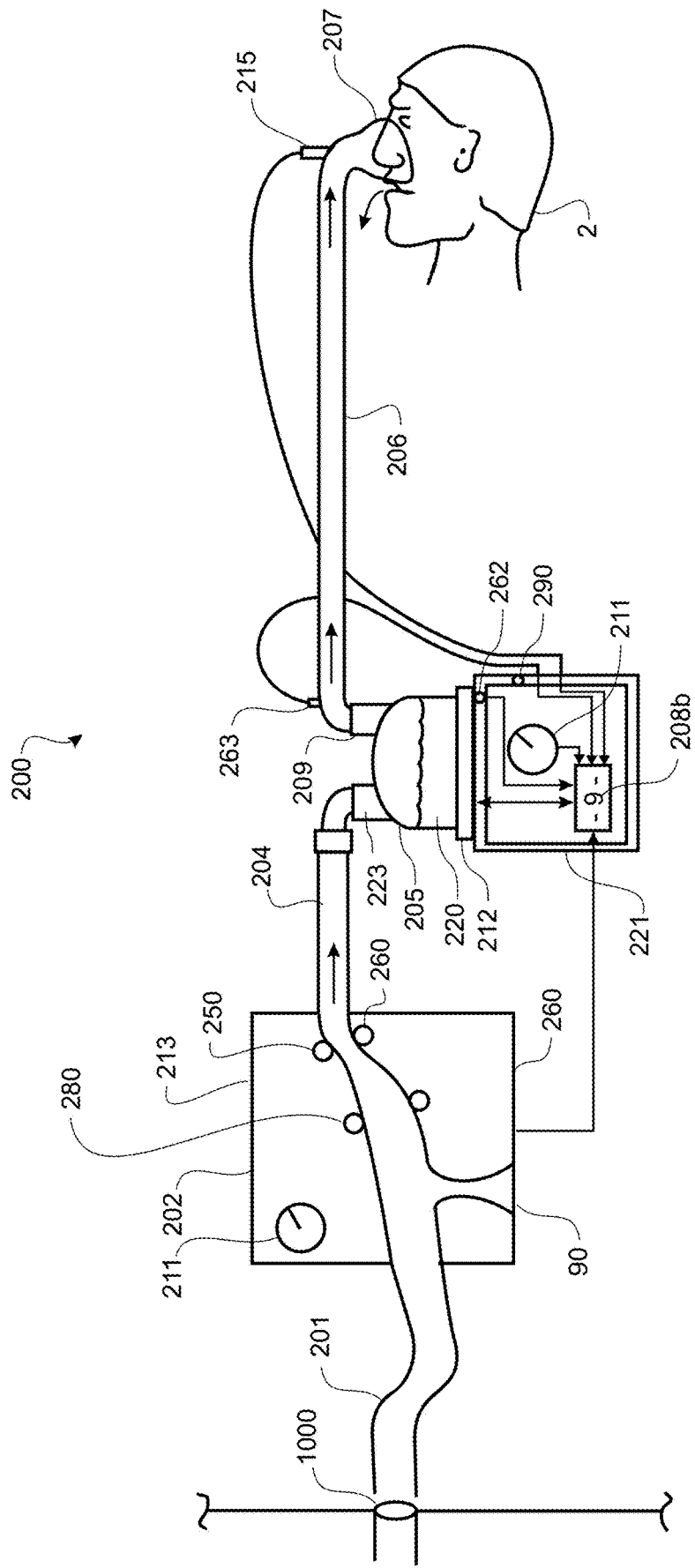
FIG. 4 shows a schematic view of a user receiving humidified air, where the user is wearing a nasal cannula, the breathing assistance system receiving gases from a central source via a wall inlet and providing these to a control unit, which provides the gases to a humidifier chamber in line with and downstream of the control unit.

The method can be used in the controller in a number of broad system configurations. By way of example, three typical system configurations are illustrated in FIGS. 2 to 4 and described below. These system configurations are illustrative but not an exhaustive account of the system configurations in which this method may be used.

Figure 2A:
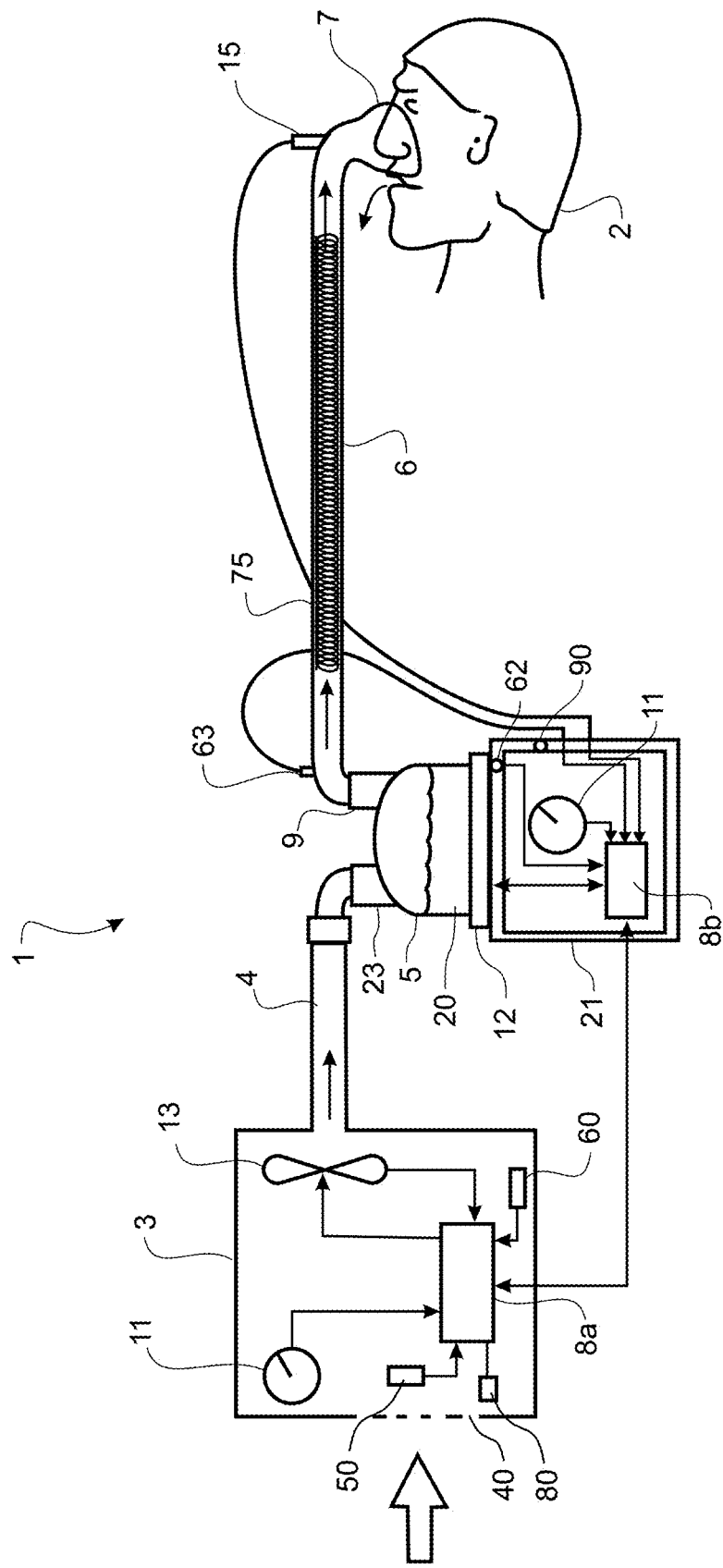
FIG. 2a shows a schematic view of a user receiving humidified air, with the user wearing a nasal mask and receiving air from a modular blower/humidifier breathing assistance system.
Figure 2B:
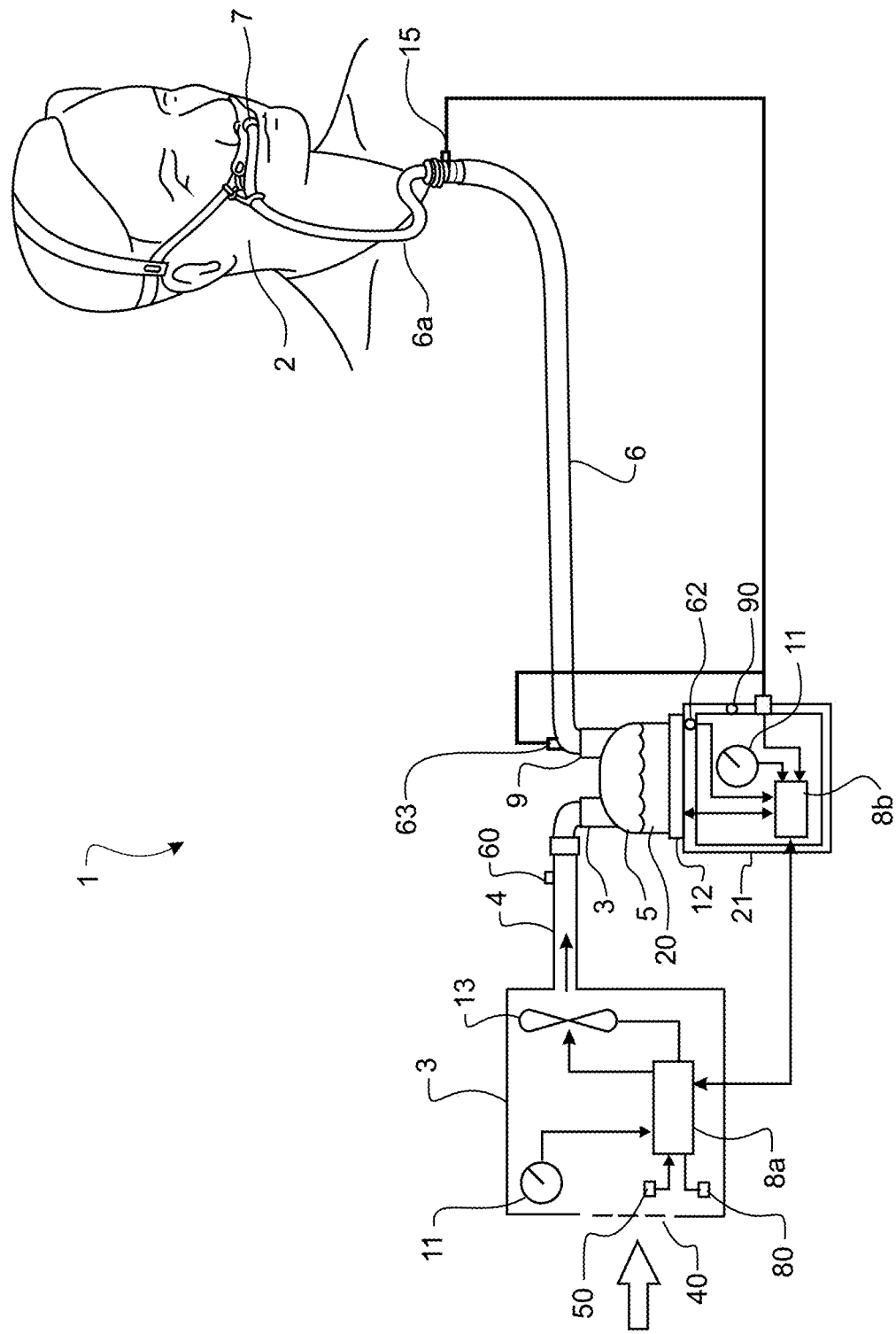
FIG. 2b shows a schematic view of a user receiving humidified air, where the user is wearing a nasal cannula and receiving air from a modular blower/humidifier breathing assistance system.

A schematic view of a user 2 receiving air from a modular assisted breathing unit and humidifier system 1 according to a first example system configuration is shown in FIGS. 2a and 2b. The system 1 provides a pressurised stream of heated, humidified gases to the user 2 for therapeutic purposes (e.g. to reduce the incidence of obstructive sleep apnea, to provide CPAP therapy, to provide humidification for therapeutic purposes, or similar). The system 1 is described in detail below.

The assisted breathing unit or blower unit 3 has an internal compressor unit, flow generator or fan unit 13—generally this could be referred to as a flow control mechanism. Air from atmosphere enters the housing of the blower unit 3 via an atmospheric inlet 40, and is drawn through the fan unit 13. The output of the fan unit 13 is adjustable—the fan speed is variable. The pressurised gases stream exits the fan unit 13 and the blower unit 3 and travels via a connection conduit 4 to a humidifier chamber 5, entering the humidifier chamber 5 via an entry port or inlet port 23.

The humidifier chamber 5 in use contains a volume of water 20. In the preferred embodiment, in use the humidifier chamber 5 is located on top of a humidifier base unit 21 which has a heater plate 12. The heater plate 12 is powered to heat the base of the chamber 5 and thus heat the contents of the chamber 5. As the water in the chamber 5 is heated it evaporates, and the gases within the humidifier chamber 5 (above the surface of the water 20) become heated and humidified. The gases stream entering the humidifier chamber 5 via inlet port 23 passes over the heated water (or through these heated, humidified gases—applicable for large chamber and flow rates) and becomes heated and humidified as it does so. The gases stream then exits the humidifier chamber 5 via an exit port or outlet port 9 and enters a delivery conduit 6.

When a 'humidifier unit' is referred to in this specification with reference to the invention, this should be taken to mean at least the chamber 5, and if appropriate, the base unit 21 and heater plate 12.

The heated, humidified gases pass along the length of the delivery conduit 6 and are provided to the patient or user 2 via a user interface 7. The conduit 6 may be heated via a heater wire (not shown) or similar to help prevent rain-out.

The user interface 7 shown in FIG. 2a is a nasal mask which surrounds and covers the nose of the user 2. However, it should be noted that a nasal cannula (as shown in FIG. 2b), full face mask, tracheostomy fitting, or any other suitable user interface could be substituted for the nasal mask shown. A central controller or control system 8 is located in either the blower casing (controller 8a) or the humidifier base unit (controller 8b). In modular systems of this type, it is preferred that a separate blower controller 8a and humidifier controller 8b are used, and it is most preferred that the controllers 8a, 8b are connected (e.g. by cables or similar) so they can communicate with one another in use.

The control system 8 receives user input signals via user controls 11 located on either the humidifier base unit 21, or on the blower unit 3, or both. In the preferred embodiments the controller 8 also receives input from sensors located at various points throughout the system 1.

Figure 7:
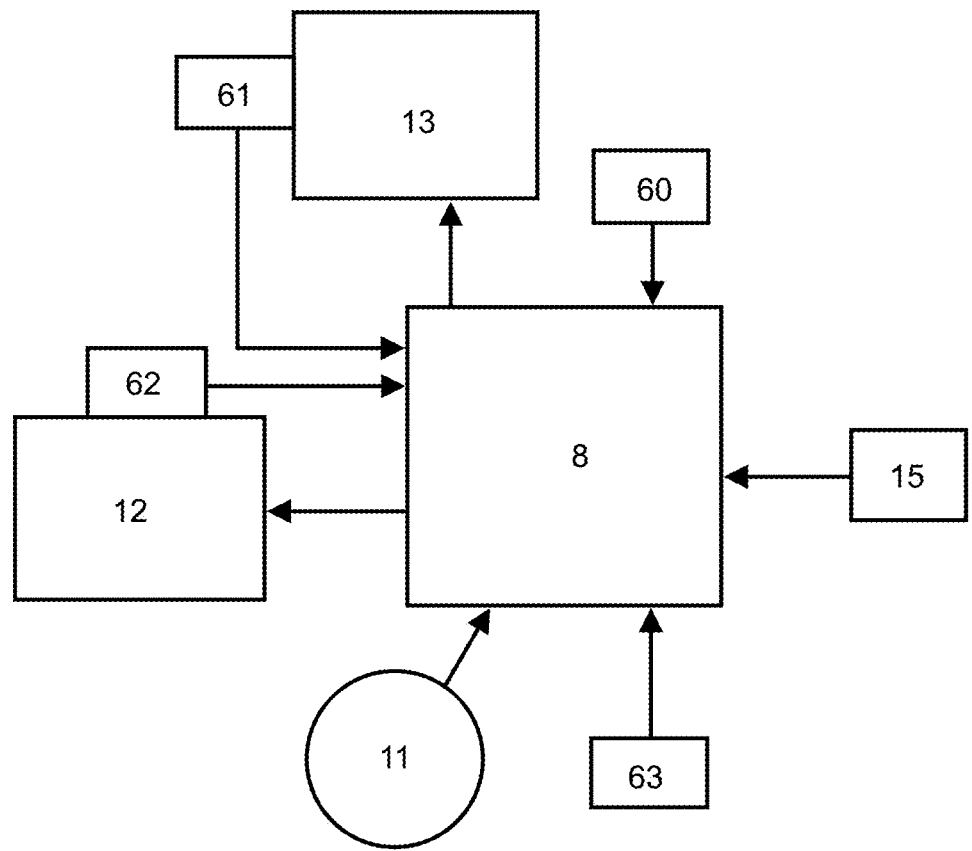
FIG. 7 shows a schematic representation of some of the connections between a controller suitable for use with the breathing assistance system of FIG. 2, 3 or 4, and other components of the preferred form of breathing assistance system as shown in FIG. 2, 3, or 4.

FIG. 7 shows a schematic representation of some of the inputs and outputs to and from the controller 8. It should be noted that not all the possible connections and inputs and outputs are shown—FIG. 7 is representative of some of the connections and is a representative example.

The sensors and their locations will be described in more detail below. In response to the user input from controls 11, and the signals received from the sensors, the control system 8 determines a control output which in the preferred embodiment sends signals to adjust the power to the humidifier chamber heater plate 12 and the speed of the fan 13. The programming which determines how the controller determines the control output will be described in more detail below.

A schematic view of the user 2 receiving air from an integrated blower/humidifier system 100 according to a second form of the invention is shown in FIG. 3. The system operates in a very similar manner to the modular system 1 shown in FIG. 2 and described above, except that the humidifier chamber 105 has been integrated with the blower unit 103 to form an integrated unit 110. A pressurised gases stream is provided by fan unit 113 located inside the casing of the integrated unit 110. The water 120 in the humidifier chamber 105 is heated by heater plate 112 (which is an integral part of the structure of the blower unit 103 in this embodiment). Air enters the humidifier chamber 105 via an entry port 123, and exits the humidifier chamber 105 via exit port 109. The gases stream is provided to the user 2 via a delivery conduit 106 and an interface 107. The controller 108 is contained within the outer shell of the integrated unit 100. User controls 111 are located on the outer surface of the unit 100.

A schematic view of the user 2 receiving air from a further form of breathing assistance system 200 is shown in FIG. 4. The system 200 can be generally characterised as a remote source system, and receives air from a remote source via a wall inlet 1000.

The wall inlet 1000 is connected via an inlet conduit 201 to a control unit 202, which receives the gases from the inlet 1000. The control unit 202 has sensors 250, 260, 280, 290 which measure the humidity, temperature and pressure and flow respectively of the incoming gases stream.

The gases flow is then provided to a humidifier chamber 205, with the gases stream heated and humidified and provided to a user in a similar manner to that outlined above. It should be noted that when 'humidifier unit' is referred to for a remote source system such as the system 200, this should be taken to mean as incorporating the control unit 202—the gases from the remote source can either be connected directly to an inlet, or via the control unit 202 (in order to reduce pressure or similar), but the control unit and the humidifier chamber should be interpreted as belonging to an overall 'humidifier unit'.

If required, the system 200 can provide $O_2$ or an $O_2$ fraction to the user, by having the central source as an $O_2$ source, or by blending atmospheric air with incoming $O_2$ from the central source via a venturi 90 or similar located in the control unit 202. It is preferred that the control unit 202 also has a valve or a similar mechanism to act as a flow control mechanism to adjust the flow rate of gases through the system 200.

Sensors

The modular and integrated systems 1, 100 and 200 shown in FIGS. 2, 3 and 4 have sensors located at points throughout the system. These will be described below in relation to the breathing assistance system 1.

The preferred form of modular system 1 as shown in FIG. 2 has at least the following sensors in the following preferred locations:

1) An ambient temperature sensor 60 located within, near, or on the blower casing, configured or adapted to measure the temperature of the incoming air from atmosphere. It is most preferred that temperature sensor 60 is located in the gases stream after (downstream of) the fan unit 13, and as close to the inlet or entry to the humidifier chamber as possible.

2) A humidifier unit exit port temperature sensor 63 located either at the chamber exit port 9, or located at the apparatus end (opposite to the patient end) of the delivery conduit 6. Outlet temperature sensor 63 is configured or adapted to measure the temperature of the gases stream as it exits chamber 5 (in either configuration the exit port temperature sensor 63 can be considered to be proximal to the chamber exit port 9).

Similarly, sensors are arranged in substantially the same locations in the integrated system 100 shown in FIG. 3 and the system 200 of FIG. 4. For example, for the integrated system of FIG. 3, an ambient temperature sensor 160 is located within the blower casing in the gases stream, just before (upstream of) the humidifier chamber entry port 123. A chamber exit port temperature sensor 163 is located either at the chamber exit port 109 and is configured to measure the temperature of the gases stream as it exits chamber 105 (in either configuration the exit port temperature sensor 163 can be considered to be proximal to the chamber exit port 109). Alternatively, this sensor can be located at the apparatus end (opposite to the patient end) of the delivery conduit 106, for either embodiment. A similar numbering system is used for the breathing assistance system shown in FIG. 4—ambient temperature sensor 260, fan unit 213, chamber exit port temperature sensor 263 located at the chamber exit port 209, etc.

It is also preferred that the breathing assistance system 1 (and 100, 200) has a heater plate temperature sensor 62 located adjacent to the heater plate 12, configured to measure the temperature of the heater plate. The breathing assistance system(s) having a heater plate temperature sensor is preferred as it gives an immediate indication of the state of the heater plate. This sensor should be in the heat path between the source of the heat and the reservoir. So, for example, a sensor on a conductive plate that contacts the water chamber on one side and has a heater on the other side is preferred.

It is also most preferred that the systems have a flow probe—flow probe 61 in system 1—located upstream of the fan unit 13 and configured to measure the gases flow. The preferred location for the flow probe is upstream of the fan unit, although the flow probe can be located downstream of the fan, or anywhere else appropriate. Again, it is preferred that a flow probe forms part of the system, but it is not absolutely necessary for a flow probe to be part of the system.

The layout and operation of the breathing assistance system 1 will now be described below in detail. The operation and layout of the systems 100 and 200 is substantially the same, and will not be described in detail except where necessary.

For the breathing assistance system 1, the readings from all of the sensors are fed back to the control system 8. The control system 8 also receives input from the user Controls 11.

Further Alternative Sensor Layouts

In a variant of the apparatus and method outlined above, the system (system 1 or system 100 or system 200) also has additional sensors as outlined below.

1) A patient end temperature sensor 15 (or 115 or 215) is located at the patient end of the delivery conduit 6 (or alternatively in or on the interface 7). That is, at or close to the patient or point of delivery. When read in this specification, 'patient end' or 'user end' should be taken to mean either close to the user end of the delivery conduit (e.g. delivery conduit 6), or in or on the patient interface 7. This applies unless a specific location is otherwise stated. In either configuration, patient end temperature sensor 15 can be considered to be at or close to the user or patient 2.

Preferred Method for Primary Water Out Determination

Figure 6:
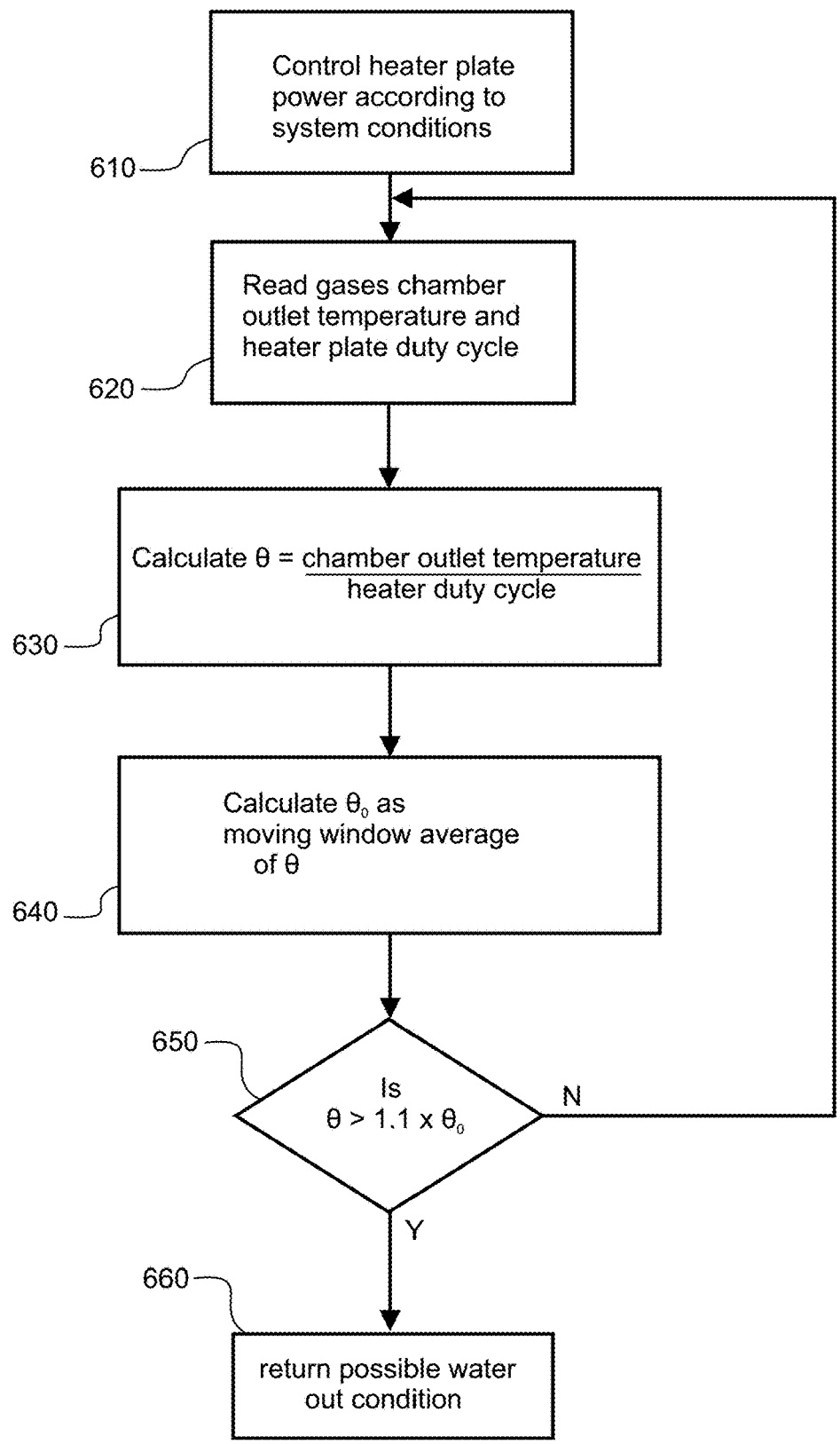
FIG. 6 is a flow diagram illustrating a preferred method to initially determine a possible water out condition.

With reference to FIG. 6, in the most preferred embodiment of the present invention the controller evaluates a function of the chamber outlet temperature and the heater plate power on a continuing basis during normal use of the apparatus. The controller determines the potential for a water out condition when the result of this function varies from a base line level. The preferred function is a ratio of the chamber outlet temperature from sensor 63 (or 163 or 263)

and the heater plate power, as represented by the heater plate duty cycle. This ratio can be represented as:

$$\Theta = \frac{CBO\_Temp}{HP\_duty\_control\ (average)}$$

where
Θ=monitoring function,
CBO_Temp=Chamber outlet temperature from sensor 63,
HP_duty_control(average)=Heater plate duty control value, recorded each second and averaged over 128 data points.

In tests conducted by the inventors, this ratio has been found to remain substantially constant in steady state conditions where water remains in the humidification chamber, but to increase when the water runs out. This was the case across a range of ambient temperatures, including ambient temperatures from 8° C. to 32° C.

In the worst case, this ratio increased by a minimum of 10% from a pre-existing base line value after the chamber ran dry.

A baseline value, $\theta_0$, may be calculated in many ways. For example, $\theta_0$ could be a moving window average of θ, or a function of a moving window average of CBO_Temp and a moving window average of the heater plate duty cycle. Alternatively, the value $\theta_0$ could be periodically updated with the present value θ, the period being, for example, 10 minutes or more.

Figure 5:
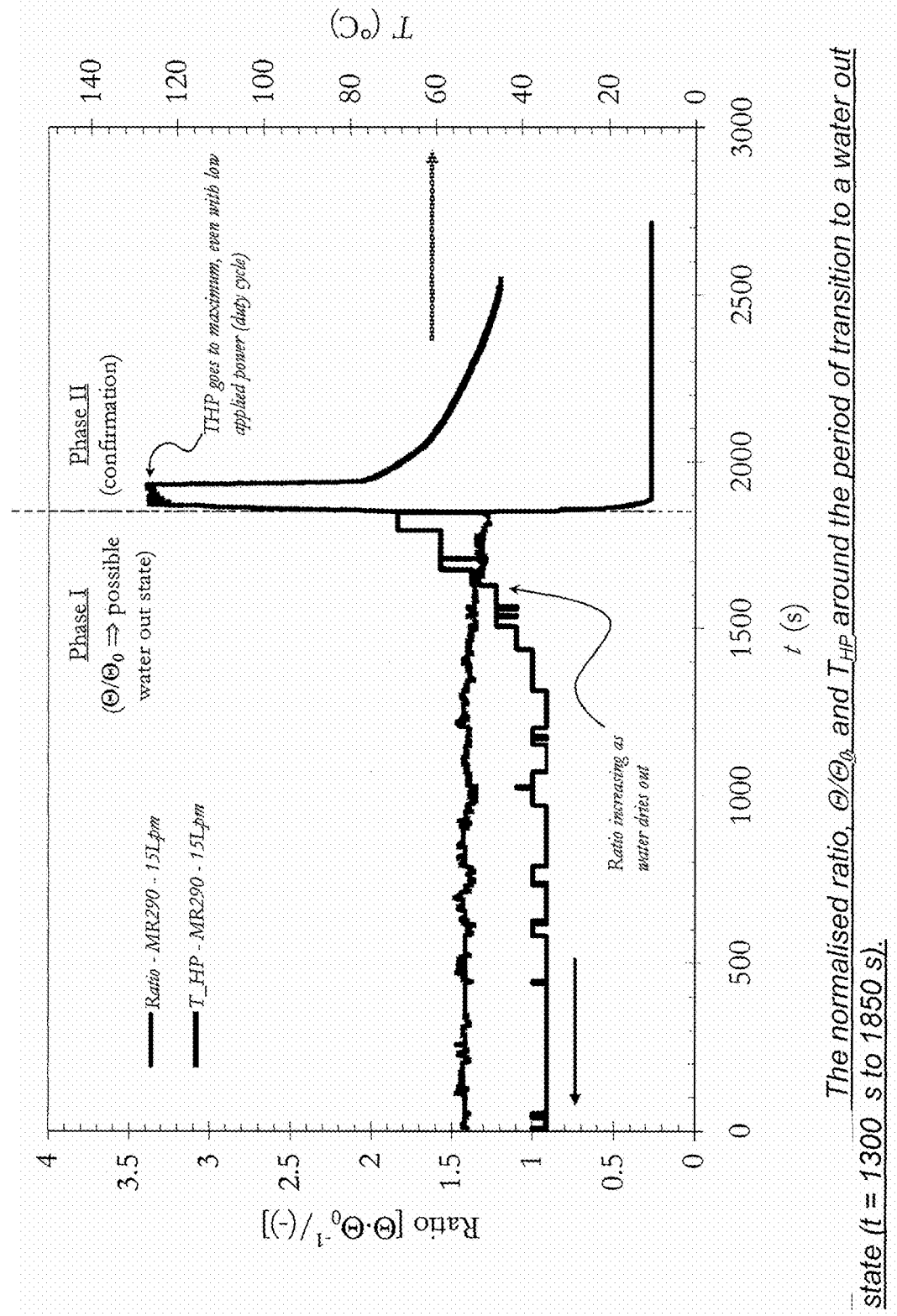
FIG. 5 is a plot against time of a function of chamber outlet temperature and heater plate power and end of heater plate temperature, according to an experiment conducted using the present invention.

An example of this monitoring function is illustrated in FIG. 5. FIG. 5 includes a plot of this preferred function against time for a Fisher & Paykel Healthcare Ltd AIRVO humidified gases delivery apparatus operating at 15 litres per minute with a Fisher & Paykel MR290 humidification chamber, and an ambient temperature of 32° C. The plot is of a normalised ratio against time and of the heater plate temperature against time. The normalised ratio is seen to remain steady until approximately t=1,300 s and then begin increasing, eventually reaching a value of approximately 1.8.

Similar testing was conducted for two different humidifier chambers used with the Fisher & Paykel Ltd AIRVO humidified gases delivery apparatus across three ambient temperatures and several flow rates. The tested conditions and flow rates represent the extreme operating conditions of the apparatus.

The normalised maximum of the evaluated ratio as the apparatus entered the water out condition is indicated in Table 1:

TABLE 1

Normalised maximum $T_{CBO}$/power ratio.

| | HP Temperature/power Ratio θ/θ₀ | | | | | |
|---|---|---|---|---|---|---|
| | 22° C. | | 32° C. | | 8° C. | |
| Chamber | 15 L min⁻¹ | 45 L min⁻¹ | 15 L min⁻¹ | 45 L min⁻¹ | 15 L min⁻¹ | 45 L min⁻¹ |
| HC360 | 2.6 | 2.5 | 1.6 | 3.0 | 1.1 | 2.9 |
| MR290 | 1.2 | 5.2 | 1.8 | 3.1 | 1.4 | 2.7 |

Within this range of conditions two typical system responses to a water out conditions were observed.

In a first type of response, the chamber outlet temperature decreased while the heater plate temperature increased to a maximum value. This was followed by the chamber outlet temperature increasing once more.

In the second type of response, the chamber outlet temperature increased directly as the water out condition occurred, but the heater plate duty control decreased while maintaining a set chamber outlet temperature. In both typical responses, the ratio of chamber outlet temperature to heater plate power increased compared to the value at the start of the water out condition. In the case of the first type of response, a longer time is required for the ratio to increase relative to the base line value than for the second type of response.

This primary water out detection method is illustrated in FIG. 6. Step 610 represents ongoing control of the heater plate power according to the system conditions. This control aims to keep the delivered gases temperature and humidity at or close to preferred levels.

As an ongoing process while this control continues, the method monitors for a possible water out condition based on a loop of steps 620 to 650.

At step 620, the method reads the chamber outlet temperature and the heater plate duty cycle. At step 630, the method calculates the ratio θ. At step 640, the method calculates $\theta_0$ as a moving window average of the most recent values of the function θ.

At step 650, the method compares the value calculated at step 630 with a multiple of the value calculated at step 640. Alternatively, the method compares the value calculated at step 630 with a value calculated at step 640 plus an arbitrary offset, namely the equation in step 650 of FIG. 6 can be $\theta > \theta_0 + \alpha$, where α is constant for all temperatures or flow rates. In the exemplary embodiment, this multiple is 1.1, which has been found a usable threshold for an initial determination of a water out condition across a range of use conditions for the humidified gases delivery apparatus tested. If the present value sufficiently exceeds the long term value, the method proceeds to step 660 and returns a possible water out condition. If the present value is less than the long term value or not significantly greater than the long term value, the method returns to step 620 and continues to monitor the gases outlet temperature and heater plate duty cycle under the normal use conditions.

The example describes an implementation using normalised values, and step 650 uses a threshold ratio. Alternatively, this step could be calculated to directly use measured values and determine a possible water out condition based on a threshold difference.

Preferred Method for Secondary Water Out Determination

According to the present invention a secondary determination of the water out condition is made in response to a primary water out determination. According to the preferred embodiment, the method takes control of the humidifier power input, adjusts the heater plate power input and observes the temperature response of the heater plate. This secondary determination is implemented to confirm the water out condition if the primary monitoring function returns a possible water out condition.

The primary monitoring function may falsely determine a water out state under certain conditions. These conditions include disturbances in the mains power supply, the occurrence of a sudden heat impulse to the chamber temperature sensor due to blocking of the flow or vigorous shaking of the unit causing water from the chamber to enter the outlet tube. These imposed increases in chamber temperature will likely lead to a decrease in heater plate duty control and hence a change to the result of the evaluation of the ratio, which could be incorrectly interpreted by the controller as a water out state.

According to the present invention, after the controller determines a primary water out condition, the control program enters a routine for performing a secondary water out determination.

Figure 8:
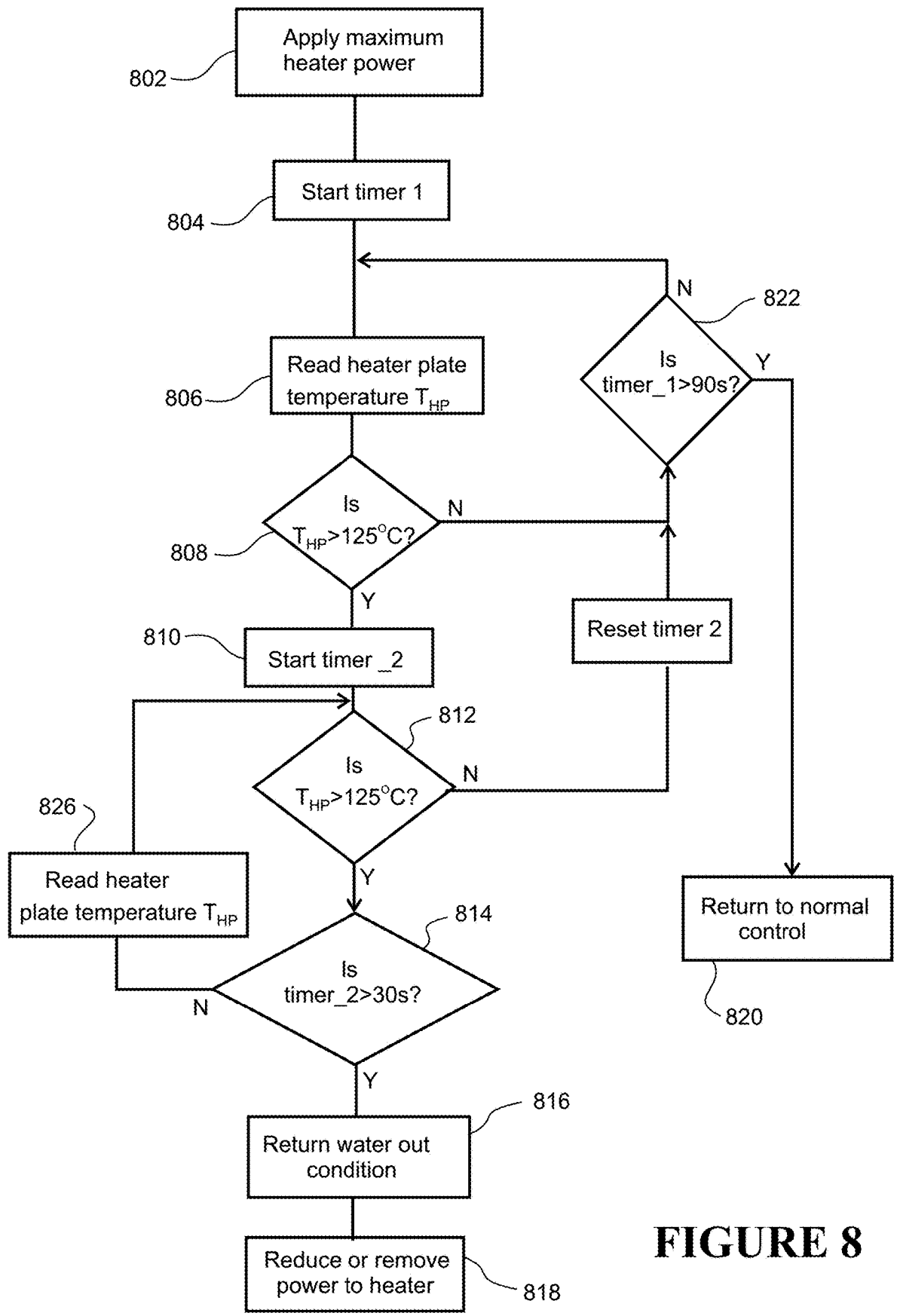
FIG. 8 is a flow diagram illustrating a confirmation method according to one embodiment of the present invention.

As illustrated in FIG. 8, according to the preferred routine, the controller increases the heater plate duty cycle to the maximum available duty cycle, applying full power to the heater plate at step 802. The control program proceeds to monitor the heater plate temperature at steps 806. and 808 until the heater plate temperature exceeds 125° C. The control program then proceeds to monitor the time for which the heater plate temperature continues to exceed 125° C. at steps 810 to 814. If the heater plate temperature continuously exceeds 125° C. for 30 s the controller determines a water out condition and sets a water out flag at step 816. The controller also reduces or removes power to the heater plate at step 818.

If the control routine does not determine a water out condition, then at step 820 the control routine returns control of the humidifier to the main operating control method. This can occur either because the heater plate temperature does not exceed 125° C. for 30 seconds within 120 seconds of applying maximum heater power at step 802. Implementing this, the method starts a first timer at step 804 and checks this timer at step 822 after determining that the temperature is not above 125° C. at step 808. If the timer is still less than 90 seconds, the method proceeds to loop back to step 806, to read the updated heater plate temperature. If the timer exceeds 90 seconds, the method proceeds from step 822 to step 820, returning to normal control.

For the other condition for returning to normal control, the method includes a check at step 812 whether the heater plate temperature is still above 125° C. In each loop, the method reads the heater plate temperature at step 826, and checks this temperature against the threshold at step 812. If the present heater plate temperature exceeds the threshold, the loop continues, otherwise the method proceeds to step 822 and checks whether 90 seconds has elapsed since step 802.

This check is illustrated in the plots of FIG. 5. The start of the secondary determination method is evident at t=1850 s. The heater plate temperature has been approximately 53° C. and slowly dropping. At t=1850 s the heater plate temperature sharply rises, rapidly reaching values above 125° C. and remaining at these elevated levels until the controller removes power from the heater plate in response to the confirmed water out condition.

Essentially this secondary confirmation applies a predetermined heater power and monitors the response of the heater plate temperature and determines whether this response is characteristic of the chamber being in a water out condition.

In the preferred method described, the applied power is the maximum available power. In some systems the applied power could be a lesser value if it has been determined that a lower power was sufficient to achieve a response that can differentiate between a water out condition and a condition where water remains in the chamber across all of the expected operating conditions of the apparatus.

According to the preferred method, the controller monitors for an increase in the heater plate temperature to a value exceeding a predetermined limit and for the heater plate temperature to remain above this limit continuously for a predetermined period of time.

Alternatively the controller could monitor for a rate of increase in the heater plate temperature that might have been shown by experimentation to be characteristic of a water out condition, or for some other characteristic of the heater plate temperature that has been determined experimentally to be characteristic of a water out condition, compared to a condition in which there is water in the chamber.

The predetermined temperature values and times described in this preferred embodiment of the present invention have been determined for a particular humidified gases delivery apparatus. For other humidified gases delivery apparatus, suitable heater plate temperature thresholds and periods would need to be determined by experimentation.

In the case of the apparatus on which this testing and experimentation was conducted, tests have shown that in a water out condition, maximum applied heater power achieves a heater plate temperature in excess of 125° C. for a consistent and continuous time. Where water remains in the humidified chamber, the heater plate temperature, with full duty cycle and in the highest ambient condition (32° C.) the heater plate temperature did not exceed 123° C. This is the worst case condition for the secondary determination, and the condition under which the secondary examination could be most likely to provide a false positive for a water out condition. Accordingly, for this device, the described secondary determination has been shown to reliably distinguish an empty chamber from a chamber with water remaining.

The invention has been described with particular reference to humidified gases delivery apparatus having a heater plate that contacts a heat conductive base of a water containing reservoir. The system of the present invention may be applied to other humidifier configurations. For example, the heater of the humidifier may reside within the water reservoir or be integrated to the base or wall of the water reservoir. In either case, the temperature sensor for the secondary determination should be influenced by both the contents of the reservoir and the heat source of the heater.

In these cases, it would be expected that the threshold temperature for the secondary determination would be lower than the threshold temperature determined experimentally for the Fisher & Paykel Healthcare Ltd AIRVO appliance.

In an appliance with a different heater arrangement, the heater temperature might be determined by a thermistor in contact with the heating element, or in contact with a heat conductive substrate in contact with the heating element. Typically there will be a maximum temperature that the substrate achieves for a given heater plate power (for example, maximum power) when there is water in the chamber due to the limiting temperature at this boundary defined by the boiling point of water. The heat supplied to the heater plate under these conditions is absorbed as latent heat of vaporisation, and does not yield a change in temperature. In the absence of water, the latent heat energy requirement disappears, and the excess energy over that required to maintain steady state temperatures gives rise to an increase in gas temperature rather than the production of water vapour.

The preferred embodiment of the present invention has been described as providing maximum power to the heater for a sustained period. The invention could be implemented so that a first elevated power is provided to the heater to bring the heater above the threshold temperature, with the power subsequently reduced to a level that maintains the temperature above the threshold temperature, but does not further elevate of the temperature of the heater plate. This could be achieved for example, by using a closed feedback loop based on heater plate temperature and could be particularly suitable where the power available to be applied to the heater plate is much larger than the power required to maintain the temperature above the threshold with temperature of the heater applied above the threshold level with only gases in the chamber.

What is claimed is:

1. An apparatus for preparing a flow of gases including:
a heater for heating a reservoir,
a temperature sensor in thermal communication with the heater to read the temperature of the heater,
a controller adapted to apply power from a power supply to the heater, the controller including a control method comprising:
monitoring system conditions during use of the apparatus,
determining a possible absence of water in the reservoir from the monitored system conditions,
following a determination of a possible absence of water, apply an amount of power from the power supply to the heater, the amount of power being:
an increase in the supplied power,
a maximum power from the power supply to the heater,
a predetermined amount of power from the power supply to the heater; or
an amount of power to the heater that would elevate the heater temperature in the absence of water, to a temperature that exceeds any temperature that the heater temperature would reach with water present in the reservoir,
monitoring an output of the temperature sensor, and
reducing the power supplied from the power supply to the heater if the monitored temperature sensor output indicates an absence of water in the reservoir.

2. The apparatus of claim 1 wherein monitoring the output of the temperature sensor includes determining a rise in heater plate temperature.

3. The apparatus of claim 1 wherein monitoring the output of the temperature sensor includes comparing the heater temperature against a threshold temperature and determining a water out condition where the monitored temperature exceeds a predetermined threshold temperature.

4. The apparatus of claim 3 wherein the controller determines the water out condition when the monitored temperature exceeds the predetermined threshold temperature by a predetermined period of time.

5. The apparatus of claim 1 wherein applying power to the heater comprises applying a maximum available power to the heater.

6. The apparatus of claim 1 wherein applying power to the heater comprises applying a predetermined amount of power to the heater.

7. The apparatus of claim 1 wherein applying power to the heater comprises applying an amount of power to the heater that would elevate the heater temperature in the absence of water to a temperature that exceeds any temperature that the heater temperature would reach with water present in the reservoir.

8. The apparatus of claim 1 wherein the heater comprises a heater plate and the apparatus includes a clamp for holding a removable chamber against the heater plate.

9. The apparatus of claim 8 wherein the temperature sensor is attached to the heater plate.

10. The apparatus of claim 1 including a blower for generating a flow of gases and a humidifier incorporating the heater and a reservoir of water, an outlet of the blower leading to an inlet of the humidifier.

11. The apparatus of claim 10 wherein the controller monitors system conditions during use of the apparatus including monitoring the temperature of gases leaving the reservoir and monitoring power applied to the heater and determines a possible water out condition based on a function of the temperature of gases leaving the humidifier and the power applied to the heater.

12. The apparatus of claim 11 wherein the function comprises a ratio of the gases temperature to the power applied to the heater.

13. The apparatus of claim 11 wherein the controller determines a possible absence of water in the reservoir by comparing a result of the function against a predetermined threshold.

14. The apparatus of claim 11 wherein the heater comprises a heater plate and wherein the function comprises a ratio of the temperature of the gases leaving the humidifier to the amount of power applied to the heater plate.

15. An apparatus for preparing a flow of gases including:
a humidifier including a reservoir and a heater for heating the reservoir,
a temperature sensor in thermal communication with the heater to read the temperature of the heater,
a controller adapted to apply power from a power supply to the heater, the controller including a control method comprising:
monitor system conditions during use of the apparatus,
determine a possible absence of water in the reservoir from the monitored system conditions,
following a determination of a possible absence of water,
applying a maximum available power from the power supply to the heater,
monitoring an output of the temperature sensor,
determining a water out condition if the output of the temperature sensor exceeds a predetermined threshold for a predetermined period of time,
subsequently reducing the power supplied from the power supply to the heater, and
providing an output indicating the water out condition.

16. The apparatus of claim 15 wherein the heater comprises a heater plate and the apparatus includes a clamp for holding a removable chamber against the heater plate.

17. The apparatus of claim 16, wherein the temperature sensor is attached to the heater plate.

18. The apparatus of claim 17 wherein monitoring the output of the temperature sensor includes determining an increase in heater plate temperature.

19. The apparatus of claim 15, further comprising a blower for generating a flow of gases, wherein the humidifier is configured to incorporate the heater and the reservoir of water, and wherein an outlet of the blower is coupled to an inlet of the humidifier.

20. The apparatus of claim 19 wherein the system conditions monitored during use of the apparatus include a temperature of gases leaving the reservoir and an amount of power applied to the heater, the controller further configured to determine the possible water out condition based on a function of the temperature of the gases leaving the humidifier and the amount of power applied to the heater.

* * * * *